(12) United States Patent
Saber et al.

(10) Patent No.: US 12,239,793 B2
(45) Date of Patent: Mar. 4, 2025

(54) DEVICE FOR REGULATING OXYGEN FOR AUTOMATED OXYGEN THERAPY

(71) Applicant: O2MATIC APS, Herlev (DK)

(72) Inventors: Farzad Saber, Bagsvaerd (DK); Ejvind Frausing Hansen, Slangerup (DK); Okan Ilker Gorgen, Frederiksberg (DK)

(73) Assignee: O2MATIC APS, Herlev (DK)

( * ) Notice: Subject to any disclaimer, the term of this patent is extended or adjusted under 35 U.S.C. 154(b) by 668 days.

(21) Appl. No.: 17/620,348

(22) PCT Filed: Jul. 9, 2020

(86) PCT No.: PCT/EP2020/069414
§ 371 (c)(1),
(2) Date: Dec. 17, 2021

(87) PCT Pub. No.: WO2021/005168
PCT Pub. Date: Jan. 14, 2021

(65) Prior Publication Data
US 2022/0339396 A1 Oct. 27, 2022

(30) Foreign Application Priority Data
Jul. 9, 2019 (DK) .............................. PA201970452

(51) Int. Cl.
*A61M 16/20* (2006.01)
*A61M 16/10* (2006.01)
(Continued)

(52) U.S. Cl.
CPC ...... *A61M 16/202* (2014.02); *A61M 16/1005* (2014.02); *G16H 20/40* (2018.01);
(Continued)

(58) Field of Classification Search
CPC ............ A61M 16/101; A61M 16/1005; A61M 2202/0208; A61M 2205/3334; A61M 16/0666; A61M 16/024; A61M 16/202
See application file for complete search history.

(56) References Cited

U.S. PATENT DOCUMENTS 5,682,877 A 11/1997 Mondry
2006/0225737 A1 10/2006 Iobbi
(Continued)

FOREIGN PATENT DOCUMENTS

WO 2006024107 A1 3/2006
WO 2006127356 A2 11/2006
WO 2019070136 A1 4/2019

OTHER PUBLICATIONS

International Search Report for PCT Application No. PCT/EP2020/069414 dated Oct. 19, 2021.
(Continued)

*Primary Examiner* — Margaret M Luarca
(74) *Attorney, Agent, or Firm* — Olive Law Group, PLLC

(57) ABSTRACT

According to the invention there is herein detailed a method for automated home oxygen therapy and a double closed-loop regulated device for regulating oxygen for automated oxygen therapy, the device and method comprising use of a controller configured for controlling the provided flow of oxygen through the valve by adjusting the valve in response to feedback from a flowmeter and a sensor; the controller configured to provide a first flow of oxygen for a first set time $t_1$ and in response to a received first set of physiological data comprising patient $SpO_2$ and pulse rate from the sensor, establish a second set time $t_2$, the controller further configured for providing a variable second flow of oxygen for the second set time $t_2$ while receiving a second set of physiological data comprising patient $SpO_2$ and pulse rate from the sensor for establishing a third set time $t_3$ based on the
(Continued)

physiological data received; and providing a third flow of oxygen for the third set time $t_3$, without feedback from the sensor.

16 Claims, 9 Drawing Sheets

(51) Int. Cl.
 *G16H 20/40* (2018.01)
 *A61M 16/00* (2006.01)
(52) U.S. Cl.
 CPC .............. *A61M 2016/0039* (2013.01); *A61M 2202/0208* (2013.01); *A61M 2205/3334* (2013.01); *A61M 2230/06* (2013.01); *A61M 2230/205* (2013.01)

(56) References Cited

U.S. PATENT DOCUMENTS

2021/0113801 A1* 4/2021 Wang ................. A61M 16/0051
2021/0361899 A1* 11/2021 Williams .......... A61M 16/1005

OTHER PUBLICATIONS

Written Opinion of the International Search Authority for PCT Application No. PCT/EP2020/069414 dated Oct. 19, 2021.

* cited by examiner

DEVICE FOR REGULATING OXYGEN FOR AUTOMATED OXYGEN THERAPY

CROSS REFERENCE TO RELATED APPLICATIONS

This application is a 35 USC 371 application of International PCT Patent Application No. PCT/EP2020/069414, filed on Jul. 9, 2020, which claims priority to Denmark Patent Application No. PA201970452, filed on Jul. 9, 2019; the contents of which are hereby incorporated by reference herein in their entireties.

TECHNICAL FIELD

With the present invention there is detailed a device for regulating oxygen for automated oxygen therapy, wherein the device can provide delivery of oxygen to homecare patients adaptive to the progress of therapy.

BACKGROUND

The control of oxygen dosing for patients admitted to hospital with hypoxemic respiratory failure has virtually been unchanged for 100 years since Haldane in 1917 described the dosing of oxygen from an oxygen tank with a manual flowmeter, a reservoir bag and a hose to a mask over the patients nose and mouth. Improvements due to the introduction of the pulse oximeter has since provided a non-invasive possibility of measuring the saturation of oxygen in the blood ($SpO_2$), however, control of oxygen flow is mostly done manually by the nursing staff after intermittent readings of patient $SpO_2$.

Depending on how critically ill the patient is, manual control of the oxygen flow is done from 2 to 24 times a day or more, and is thus a very time-consuming task. Furthermore, the intermittent and manual prescribing and administration of oxygen is often not in adherence with treatment guidelines, which for many diseases prescribe adjustment to a patient oxygen $SpO_2$ regimen without occurrence of hypoxemia (low $SpO_2$) nor hyperoxia (high $SpO_2$). Particularly, when manual $SpO_2$ control is too infrequent, repeated hypoxemia or hyperoxia can occur.

In Chronic Obstructive Pulmonary Disease (COPD) both hypoxemia and hyperoxia have been shown to increase mortality during hospitalization and to increase the risk of serious adverse events, such as respiratory failure with $CO_2$-retention in the blood and need for mechanical ventilation.

In the current market, few devices exist for automated oxygen delivery. One such device is detailed in U.S. Pat. No. 9,364,623 B2, wherein is detailed a method for administering a gas containing oxygen to a patient, the method including: measuring an oxygen-dependent physiological parameter in the patient; establishing an optimal gas delivery parameter based on the oxygen-dependent parameter; and administering the gas to the patient in accordance with the optimal gas delivery parameter, optionally wherein the method further includes monitoring the oxygen-dependent physiological parameter. Patent application WO 2017059530 A1 details further developments of the methods detailed in U.S. Pat. No. 9,364,623.

According to the description in U.S. Pat. No. 9,364,623, the device for executing the method regulates the flow of oxygen using a double closed-loop feedback system, which is generally known from the prior art, cf. e.g. WO 2006/110812.

Applicant markets a device for regulating oxygen in automated oxygen therapy, O2matic, based on the technology detailed in WO 2006/110812 for continuous patient use in hospitals and care stations.

In WO 2006/110812 (cf. FIG. 1) there is detailed a device (1) and method for limiting adverse events during supplemental oxygen therapy, wherein the oxygen flow between a patient (4) and an oxygen source (2) is controlled with a valve (11), such as a proportional solenoid capable of constraining flowrates within a continuous range. The flowrate of oxygen is accurately controlled in a double closed-loop regulation comprising flowrate measurements (12) and continuous measurements (3) of vital patient's physiological data for automatically establishing an optimum therapeutic oxygen flowrate. During use, controller signal filtering is provided for improving the overall response and stability, wherein the control algorithm varies flowrates to minimize disturbances in the patient feedback measurements and the double-loop feedback allows the system to settle iteratively on a stable value for the oxygen supply to the patient.

The present invention relates to improvements to control algorithms for oxygen flowrates of the prior art, for implementation into double closed-loop regulated devices for automated oxygen therapy, whereby the devices of the prior art become suitable for homecare therapy and outpatient management of chronic disease.

It is a persistent problem of current homecare therapy oxygen-delivery devices that, either the oxygen regulation is inadequate due to high requirements on manual regulation, or (due to restrictions to personal mobility from continuous attachment to a sensor) patient compliance is significantly reduced, both situations causing inadequate patient treatment.

In particular, current oxygen therapy at home is mostly based on providing a substantially constant flow of oxygen to the patient at need, thereby reducing the control over the $SpO_2$-levels of the blood, which substantially constant flow of oxygen is regulated on occasions where the patient receiving therapy at home is visited and assessed, e.g. by measurements, by authorized health care personnel. However, as home visits in modern health care are becoming increasingly sparse, intervals between events of manual oxygen flow regulation are increasing. Further, the time needed for proper assessment of a patient's physiological state seldom correlates with scheduled lengths of visits. Accordingly, automated oxygen therapy at home is not currently offered to patients for concerns that patients may receive inadequate or even incorrect oxygen therapy during most of the time spent in automated treatment.

Systems for home oxygen therapy based on the prior art devices of WO 2006/110812 and aiming at improving patient compliance and the quality of outpatient therapy have been detailed e.g. in WO 2016/156634 A1 or WO 2016/106299 A1. In WO 2016/156634 the double closed-loop regulation devices of the prior art is sought improved by additional communication means for communicating with a care-station unit for improved regulation of oxygen delivery, whereas in WO 2016/106229 use of an alternative sensor to the pulse oximeter is detailed, which sensor is continuously arranged on the torso of the patient while the patient is at home. A drawback of the sensor in WO 2016/106229 compared to the pulse oximeter is that the sensor of WO 2016/106229 requires skilled personnel for changing, e.g. for bathing of the patient, and thereby some of the benefits of outpatient treatment to hospitalized treatment are lost. In both disclosures, the drawback of substantially constant oxygen flow is sought overcome by improving e.g. the sensor required for the double closed-loop regulation of oxygen.

However, as patients within the patient group relevant for outpatient oxygen therapy often suffer from multiple medical conditions, the present inventors have found that outpatient oxygen therapy reliant on continuous sensing of a patient's physiological data is inconvenient or inadequate for providing oxygen therapy to this patient group, particularly due to limitations on patient mobility. Hence, compliance is reduced, as most patients will not accept wearing continuous monitoring equipment. And, while the present invention is not limited in its use to such patient groups, the inventors have found that advances in treatment has to be equally accompanied with improvements to treatment compliance and ease of therapy not currently present in the art. The present invention builds on this realization.

SUMMARY OF THE INVENTION

According to a first aspect of the invention there is herein detailed a double closed-loop regulated device (10) for regulating a flow of oxygen for automated oxygen therapy, the device (10) comprising an oxygen flow path (5a-c) for passing a flow of oxygen from a source of oxygen (2) via the device (10) for providing a controlled flow of oxygen, the device (10) further comprising a valve (11) and a flowmeter (12) arranged consecutively on the oxygen flow path (5a-c), and a controller (13) configured (15) for controlling the flow of oxygen through the valve (11) by adjusting the valve (11) in response to feedback (16,31) from the flowmeter (12) and a sensor (3) for measuring sets of physiological data comprising patient $SpO_2$ and pulse rate, the sensor (3) configured for being operatively connected (31) to the controller (13); the controller further configured for providing (100) a first flow of oxygen for a first set time $t_1$ and in response to a received first set of physiological data comprising patient $SpO_2$ and pulse rate from the sensor (3), establishing (200) a second set time $t_2$, the controller (13) further configured for providing (300) a variable second flow of oxygen for the second set time $t_2$ while receiving a second set of physiological data comprising patient $SpO_2$ and pulse rate from the sensor (3) for establishing (400) a third set time $t_3$ in response to the second set of physiological data received; and providing (500) a third flow of oxygen for the third set time $t_3$ without receiving feedback (31) from the sensor (3).

According to an embodiment of the first aspect of the invention there is herein detailed a double closed-loop regulated device (10) for regulating a flow of oxygen for automated oxygen therapy wherein $t_1+t_2<t_3$.

According to an embodiment of the first aspect of the invention there is herein detailed a double closed-loop regulated device (10) for regulating a flow of oxygen for automated oxygen therapy, the device (10) further comprising a sensor (3) operatively connected (31) to the controller (13), preferably wherein the sensor (3) is a pulse oximeter.

According to an embodiment of the first aspect of the invention there is herein detailed a double closed-loop regulated device (10) for regulating a flow of oxygen for automated oxygen therapy, wherein the controller (13) is configured for returning an error (102) of process during execution of a method (20) for providing automated oxygen therapy to a patient according to a method of the invention, if a criterion for error is passed.

According to an embodiment of the first aspect of the invention there is herein detailed a double closed-loop regulated device (10) for regulating a flow of oxygen for automated oxygen therapy, wherein the device (10) further comprises notification means (17) operatively connected to the controller (13) and configured for providing a notification in the event of an error (102) of process.

According to an embodiment of the first aspect of the invention there is herein detailed a double closed-loop regulated device (10) for regulating a flow of oxygen for automated oxygen therapy, wherein the device (10) further comprises patient data input means (18) operatively connected to the controller (13) for permitting (18a) patient data to be provided to the controller (13) for configuring the controller for establishing at least one value of t, $t_1$, $t_2$, or $t_3$ and/or for establishing at least one of a first, a second or a third flow of oxygen.

According to an embodiment of the first aspect of the invention there is herein detailed a double closed-loop regulated device (10) for regulating a flow of oxygen for automated oxygen therapy, wherein the device (10) further comprises a memory unit (19) operatively connected to the controller (13) for permitting provided patient data to be stored and accessed by the controller (13).

According to a second aspect of the invention there is herein detailed a method (20) for providing automated oxygen therapy to a patient (4) comprising: providing (100) the patient (4) with a first flow of oxygen for a first set time $t_1$ by providing a flow of oxygen from a source of oxygen (2) via an oxygen flow path (5a-c) comprised in a double closed-loop regulated device (10) for regulating oxygen for automated oxygen therapy; the device (10) further comprising a valve (11) and a flowmeter (12) arranged consecutively on the oxygen flow path (5a-c), and a controller (13) configured (15) for controlling the flow of oxygen through the valve (11) by adjusting the valve (11) in response to feedback (16,31) from the flowmeter (12) and a sensor (3) configured for measuring sets of physiological data comprising patient $SpO_2$ and pulse rate, the sensor (3) operatively connected (31) to the controller (13); wherein during the first set time $t_1$ the sensor (3) provides to the controller (13) a first set of physiological data for the patient (4) comprising patient $SpO_2$ and pulse rate for establishing (200) a second set time $t_2$ based on the physiological data received by the controller (13); providing (300) the patient (4) with a variable second flow of oxygen for the established second set time $t_2$ while the sensor (3) is providing the controller (13) with a second set of physiological data for the patient (4) comprising patient $SpO_2$ and pulse rate for establishing (400) a third set time $t_3$ based on the physiological data received by the controller (13); and providing (500) the patient (4) with a third flow of oxygen for the established third set time $t_3$, without receiving feedback (31) from the sensor (3).

In an embodiment thereof, $t_1+t_2<t_3$.

According to an embodiment of the second aspect of the invention there is herein detailed a method (20) for providing automated oxygen therapy to a patient (4), wherein the patient (4) shall be provided (100) with a first flow of oxygen for a first set time, $t_1$, during which time, $t_1$, the patient receiving treatment wears a sensor (3) providing patient physiological data to the controller (13).

According to an embodiment of the second aspect of the invention there is herein detailed a method (20) for providing automated oxygen therapy to a patient (4), wherein the first set time, $t_1$, does not exceed 15 minutes, does not exceed 10 minutes, does not exceed 9 minutes, does not exceed 8 minutes, does not exceed 7 minutes, preferably does not exceed 6 minutes, and more preferably does not exceed 5 minutes.

According to an embodiment of the second aspect of the invention there is herein detailed a method (20) for providing automated oxygen therapy to a patient (4), wherein the provided second flow of oxygen for the second set time, $t_2$, is an iterative second flow of oxygen during at least a part of the second set time, $t_2$.

According to an embodiment of the second aspect of the invention there is herein detailed a method (20) for providing automated oxygen therapy to a patient (4), wherein the second set time, $t_2$, does not exceed 30 minutes, does not exceed 25 minutes, does not exceed 22 minutes, does not exceed 20 minutes, does not exceed 19 minutes, does not exceed 18 minutes, does not exceed 17 minutes, preferably does not exceed 16 minutes, and more preferably does not exceed 15 minutes.

According to an embodiment of the second aspect of the invention there is herein detailed a method (20) for providing automated oxygen therapy to a patient (4), wherein a total measurement period, $t_1+t_2$, does not exceed 30 minutes, does not exceed 25 minutes, does not exceed 20 minutes, does not exceed 18 minutes, does not exceed 16 minutes, does not exceed 15 minutes, does not exceed 14 minutes, preferably does not exceed 12 minutes, and more preferably does not exceed 10 minutes.

According to an embodiment of the second aspect of the invention there is herein detailed a method (20) for providing automated oxygen therapy to a patient (4), wherein the patient (4) shall be provided (500) with a third flow of oxygen for a third set time, $t_3$, during which time, $t_3$, it is not necessary for the patient receiving treatment to wear a sensor (3) providing patient physiological data to the controller (13).

According to an embodiment of the second aspect of the invention there is herein detailed a method (20) for providing automated oxygen therapy to a patient (4), wherein third set time, $t_3$, permits a thrice daily measurement period, $t_1+t_2$, more preferably permits a twice daily measurement period, $t_1+t_2$, or even more preferably permits a once daily measurement period, $t_1+t_2$.

According to an embodiment of the second aspect of the invention there is herein detailed a method (20) for providing automated oxygen therapy to a patient (4), wherein anyone of a first, a second and/or a third flow of oxygen does not exceed 5 l/min for more than 1 hour.

DETAILED DESCRIPTION

The aspects and embodiments of the invention shown in the figures are exemplary of the invention, and shall not be construed as limiting the invention thereby. In the figures, like numbers correspond to like elements.

Figure 1:
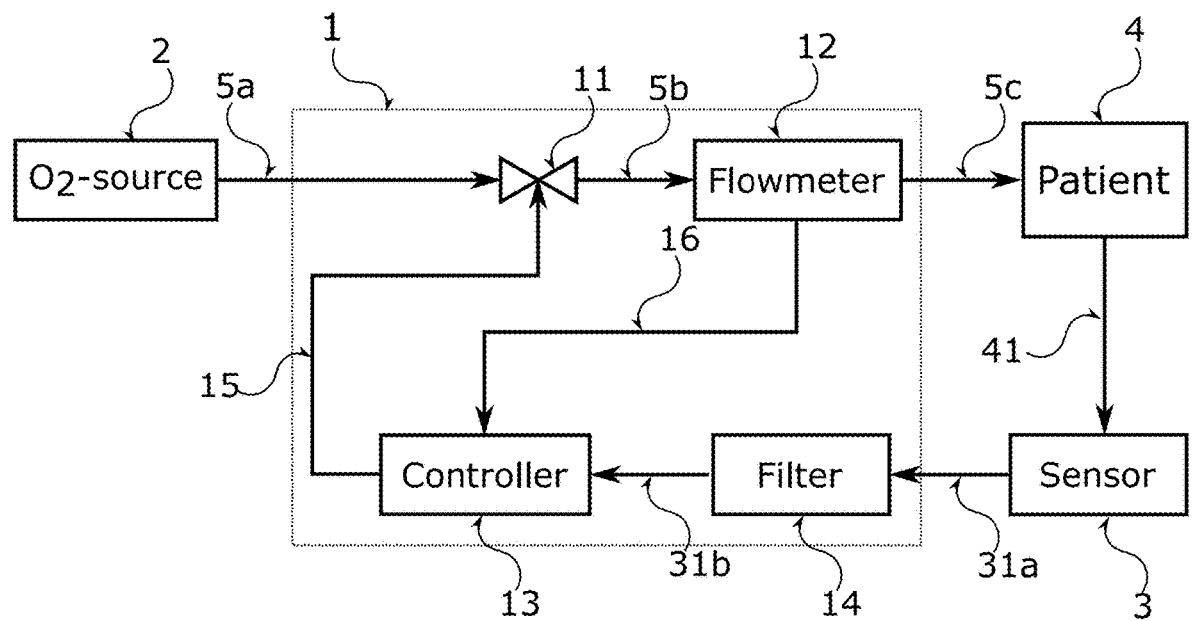
FIG. 1: Prior art device for automated oxygen therapy

In FIG. 1 there is shown (as detailed in WO 2006/110812) a double closed-loop regulated device (1) for regulating oxygen for automated oxygen therapy comprising an adjustable valve (11) for regulating a flow of oxygen, a flowmeter (12) for measuring a flow of oxygen, a controller (13) configured (15) for controlling a flow of oxygen through the valve (11) by adjusting the valve; the valve (11) and flowmeter (12) arranged consecutively for providing a flowpath for oxygen (5a-c) through the device (1) such that, in use, oxygen from an oxygen source (2) can be provided to a point of use, such as being provided to a patient (4), via the device (1); wherein the flowmeter (12) is configured (16) for, in response to a flow of oxygen set by the controller (13), providing a first closed-loop feedback signal to the controller (13) comprising information on the measured flow of oxygen, for adjusting the valve (11) to provide a predetermined flow of oxygen; the controller (13) further configured (31a-b) for receiving a second closed-loop feedback signal from a sensor (3) configured (41) for measuring, in use of the device (1), a physiological data of a patient (4) receiving oxygen at the point of use, and providing the physiological data of the patient (4) to the controller as the second closed-loop feedback signal, optionally via a filter (14) conditioning the second closed-loop feedback signal; whereby the controller (13) in response to the second closed-loop signal comprising the physiological data of the patient (4) adjusts the predetermined flow of oxygen iteratively until the measured physiological data of the patient (4) corresponds to preset physiological data for the patient (4).

In the double closed-loop regulated device (1) for regulating oxygen for automated oxygen therapy detailed in WO 2006/110812 the presence of a filter (14) was considered necessary for conditioning the signal comprising the measured physiological data of the patient in order to obtain a true measured physiological data from the sensor, the sensor in WO 2006/110812 preferably being a pulse oximeter. In the double closed-loop regulated devices for regulating oxygen for automated oxygen therapy of the present invention, a filter may or may not be present depending on the quality of the signal comprising the physiological data of a patient received from the sensor during automated oxygen therapy.

Figure 2:
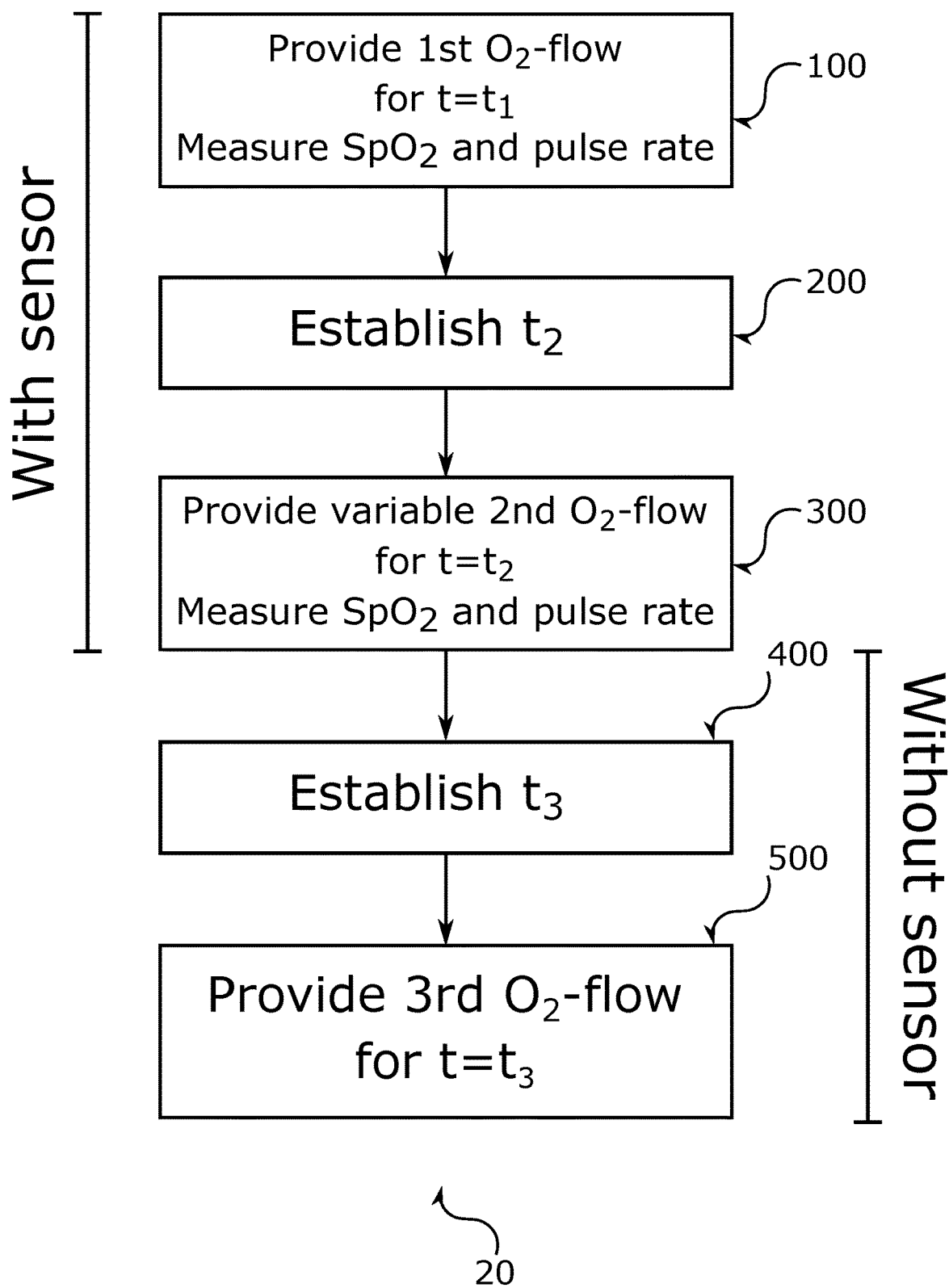
FIG. 2: Concept for automated home oxygen therapy

In FIG. 2 there is detailed the basic concept and method (20) for providing automated home oxygen therapy using a double closed-loop regulated device (1) of the present invention in its broadest aspect.

According to the invention, there is disclosed in a first aspect a method (20) for providing automated oxygen therapy to a patient (4) comprising: providing (100) the patient (4) with a first flow of oxygen for a first set time $t_1$ by providing oxygen from a source of oxygen (2) via an oxygen flow path (5a-c) comprised in a double closed-loop regulated device (10) for regulating oxygen for automated oxygen therapy; the device (10) further comprising a valve (11) and a flowmeter (12) arranged consecutively on the oxygen flow path (5a-c), and a controller (13) configured (15) for controlling a provided flow of oxygen through the valve (11) by adjusting the valve (11) in response to feedback (16,31) from the flowmeter (12) and a sensor (3) configured for measuring sets of physiological data comprising patient $SpO_2$ and pulse rate, the sensor (3) operatively connected (31) to the controller (13); wherein during the first set time $t_1$ the sensor (3) provides to the controller (13) a first set of physiological data for the patient (4) comprising patient $SpO_2$ and pulse rate for establishing (200) by the controller (13) a second set time $t_2$ based on the physiological data received by the controller (13); providing (300) the patient (4) with a variable second flow of oxygen for the established second set time $t_2$ while the sensor (3) is providing the controller (13) with a second set of physiological data for the patient (4) comprising patient $SpO_2$ and pulse rate for establishing (400) by the controller (13) a third set time $t_3$ based on the physiological data received by the controller (13); and providing (500) the patient (4) with a third flow of oxygen for the established third set time $t_3$, without receiving feedback (31) from the sensor (3). In a preferred embodiment thereof $t_1+t_2<t_3$.

The underlying concept for the method is, that by having two, comparatively short periods of measuring patients' physiological data using the sensor (3) (comparative to a third and longer treatment period with oxygen), where in each period, the oxygen flow is differently regulated, an improved prediction for the necessary oxygen flow in the third and longer treatment period with oxygen can be made. Here, the improved prediction is sufficient for reducing the risk of treatment (by not having continuous oxygen flow regulation based on continuous sensing of physiological patient data concomitant with iterative oxygen flow regulation) to a level, which is lower than the current risk of treatment associated with irregular oxygen flow adjustments by visiting health care personnel, thereby providing improvements to patient's overall health.

Figure 3:
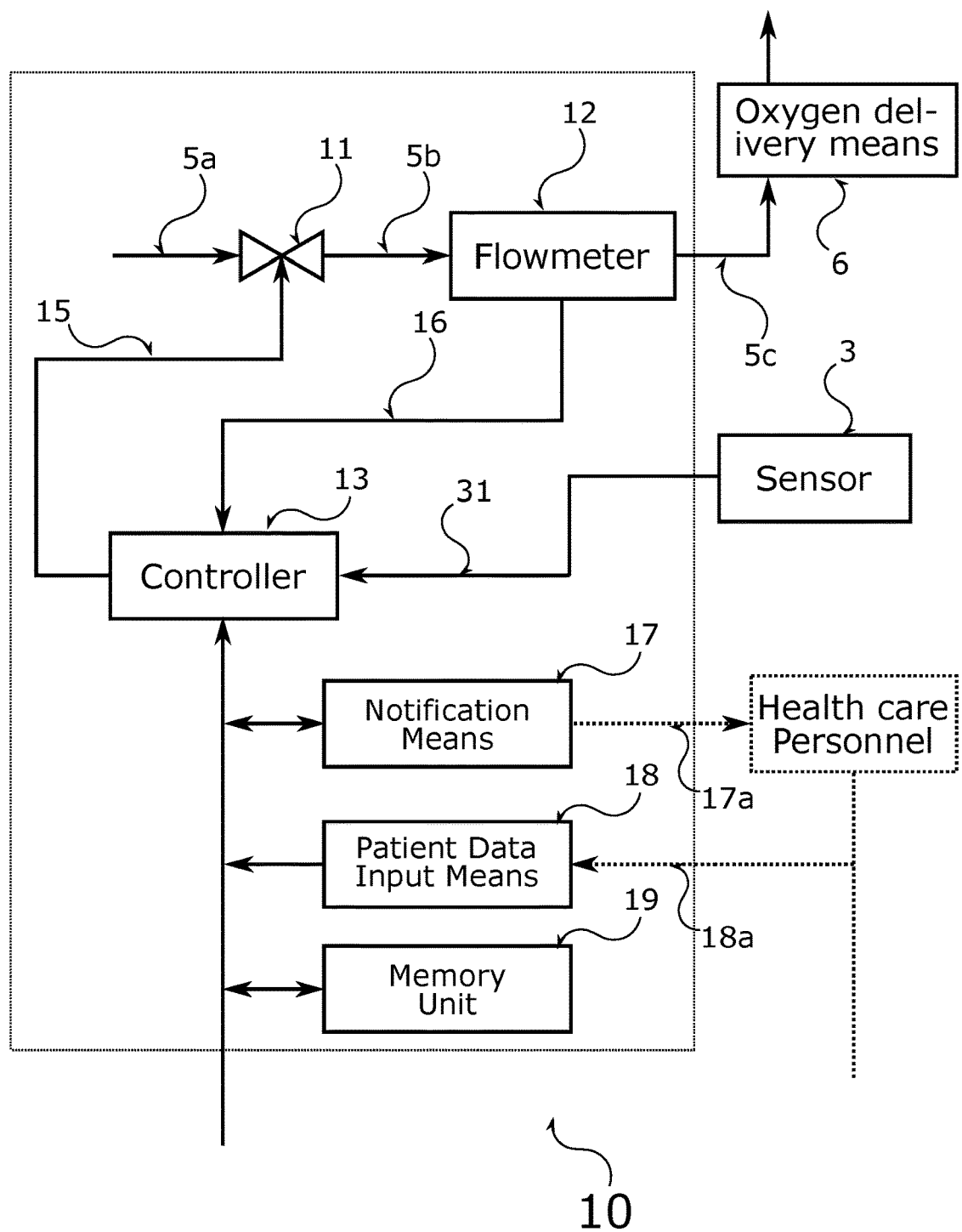
FIG. 3: Device for automated home oxygen therapy of the invention

Further, and according to the invention, there is disclosed in a second aspect a double closed-loop regulated device (10) for regulating oxygen for automated oxygen therapy, the device (10) comprising an oxygen flow path (5a-c) for passing a provided flow of oxygen from a source of oxygen (2) via the device (1) for providing a controlled flow of oxygen, the device (1) further comprising a valve (11) and a flowmeter (12) arranged consecutively on the oxygen flow path (5a-c), and a controller (13) configured (15) for controlling the provided flow of oxygen through the valve (11) by adjusting the valve (11) in response to feedback (16,31) from the flowmeter (12) and a sensor (3) configured for measuring sets of physiological data comprising patient $SpO_2$ and pulse rate, the sensor (3) for being operatively connected (31) to the controller (13); the controller configured to provide (100) a first flow of oxygen for a first set time $t_1$ and in response to a received first set of physiological data comprising patient $SpO_2$ and pulse rate from the sensor (3), establish (200) a second set time $t_2$, the controller (13) further configured for providing (300) a variable second flow of oxygen for the established second set time $t_2$ while receiving a second set of physiological data comprising patient $SpO_2$ and pulse rate from the sensor (3) for establishing (400) a third set time $t_3$ based on the physiological data received; and providing (500) a third flow of oxygen for the established third set time $t_3$, without receiving feedback (31) from the sensor (3). In a preferred embodiment thereof, $t_1+t_2<t_3$. The device (10) of the invention and embodiments thereof are exemplarily illustrated in FIG. 3.

As is custom in the art, oxygen delivery means (6) are usually required for proper delivery of a flow of oxygen to a patient (4), such as oxygen masks, nasal oxygen cannulas etc., the oxygen delivery means (6) comprised in the oxygen flow path downstream (5c) of the flowmeter (12). Such oxygen delivery means (6) are in general known to the skilled person and are employed, in relation to the present invention, as known in the art. In some embodiments of the present device (10), oxygen delivery means (6) may be comprised in the device. However, normally the device (10) of the invention is configured for being operatively connected to oxygen delivery means (6), which thereby can be easily replaced for patient safety and hygiene.

In preferred embodiments of the method (20) and device (10) of the invention, the sensor (3) is a pulse oximeter.

In preferred embodiments, the device (10) of the invention comprises a sensor (3) operatively connected (31) to the controller (13). In even more preferred embodiments thereof, the sensor (3) is a pulse oximeter.

In an embodiment of the double closed-loop regulated device (10) for regulating a flow of oxygen for automated oxygen therapy, the controller (13) is configured for returning an error (102) of process if a criterion for error (102) of process is passed.

In an embodiment of the method (20) and device (10), the controller (13) is configured for returning an error (102) of process during execution of the method (20) of the invention, if a criterion for error is passed. Exemplary, but non-limiting, embodiments detailing criteria for error (102) of process are detailed herein. In a preferred embodiment of the controller configured for returning and error (102) of process, the controller (13) is further configured for providing information of a returned error (102) of process to notification means (17) comprised in the device (10) of the invention. By having the controller (13) configured for returning errors in the executed processes of the invention to notification means, safety in outpatient treatment is enhanced.

Accordingly, in one embodiment of the device (10) of the invention, the device (10) comprises notification means (17) operatively connected to the controller (13) and configured for providing a notification in the event of an error (102) of process.

In one embodiment of the notification means (17) configured for providing a notification in the event of an error (102) of process, the notification means (17) is configured (17a) for contacting authorized health care personnel. Such notification can e.g. comprise an automated email or call notification to a ward in charge of home therapy. In general, the construction and implementation of notification means (17) for health care and in health care devices are considered within the skills of the person in the art and outside the scope of the present invention.

In an embodiment of the device (10) of the invention, the device (10) comprises patient data input means (18) operatively connected to the controller (13) for permitting (18a) authorized health care personnel to provide patient data, such as e.g. patient treatment data or expected patient physiological data, to the controller (13) for configuring the controller for establishing at least one value of t, $t_1$, $t_2$, or $t_3$ and/or for establishing at least one of a first, a second or a third flow of oxygen. In an embodiment, all values of t, $t_1$, $t_2$, or $t_3$ and/or the first, the second or the third flow of oxygen are established by patient data input by authorized health care personnel. This may e.g. be necessary in connection with a notification of error received by the health care personnel for overriding eventual controller established values of t, $t_1$, $t_2$, or $t_3$ and/or the first, the second or the third flow of oxygen until health care personnel can perform a recalibration or restart of the device (10).

In an embodiment of the device (10) of the invention, the device (10) comprises a memory unit (19) operatively connected to the controller (13) for permitting provided patient data, such as e.g. patient treatment data or expected patient physiological data, to be stored and accessed by the controller (13).

As discussed, the present inventors have found that outpatient or home oxygen therapy reliant on continuous sensing of a patient's physiological data is not feasible for providing adequate oxygen therapy to the patient groups most advantageously treated in outpatient oxygen therapy, in particular because the mobility restrictions necessitated by having continuous measurements taken of physiological patient data lead to decreased treatment compliance in the relevant patient group.

The present invention therefore aims at reducing the necessity for continuous measurements of patient physiological data to a minimum time necessary for providing adequate predictive value for a given patient undergoing treatment in accordance with the invention, such that the majority of treatment can be performed without requiring measuring the patient's physiological data such as e.g. $SpO_2$ and pulse rate.

To this purpose, the present inventors have advantageously and surprisingly found that minimization can be obtained of the time necessary for measuring a patient's physiological data and providing a predictive flow of oxygen during a period of time, wherein the patient is not measuring his or hers physiological data, if rather than simply providing a single shortened measuring phase for providing a prediction on the necessary oxygen flow when not measuring, the measuring phase with sensor is split into at least a first and a second separate measuring phases, each operative for a respective given length of time, $t_1$ or $t_2$.

Clinically, it has been established that oxygen flow supplied to a human should not exceed 5 liters per minute (1/min), preferably should not exceed 4.5 l/min for more than one hour. While treatment using oxygen flow rates in excess of 5 liters per minute (1/min) per se has a low risk for unwanted side effects of treatment (contrary to too low oxygen flow), there are associated and unwanted side effects due to a too high oxygen flow, such as dryness in the mouth, which are preferably to avoid. However, both healthy humans as well as persons suffering from e.g. COPD are at risk from hypercapnia if oxygen saturation in the blood stream prevents adequate release of carbon dioxide from the cells. Accordingly, the controller in preferred embodiments is configured for restricting the oxygen flow rate to maximum 5 l/min. Further, the controller (13) in some preferred embodiments is configured for lowering a respective first, second and/or third flow of oxygen to below 4.5 l/min if the respective flow of oxygen has exceeded 4.5 l/min for more than one hour. In embodiments thereof, the controller (13) is further configured for notifying health care personnel, preferably notifying health care personnel using notification means (17) comprised in the device (10) of the invention.

Apart from this particular upper limit on the oxygen flow, no specific limitations needs to be in place for the respective first, second and/or third oxygen flows in the method of the invention, due to the adaptive oxygen flow regulation resulting from concomitant oxygen flow regulation based on the measured patient physical data during the respective first and second measurement phases, defined by $t_1$ and $t_2$, respectively.

Nevertheless, for patient safety, if a respective first, second and/or third oxygen flow is below a given necessary oxygen flow for a given patient, in some preferred embodiments the controller (13) is configured for increasing the oxygen flow to 4.5 l/min and to notify health care personnel, preferably notifying health care personnel using notification means (17) comprised in the device (10) of the invention.

In general, it is for a medical practitioner to determine lower and upper limits for the oxygen flow rate during a treatment phase, $t_1$, $t_2$ and/or $t_3$. In embodiments of the invention, the controller (13) is configured for receiving, preferably receiving as input patient data, requisite lower and upper limits for the oxygen flow rate during any of the treatment phases, $t_1$, $t_2$ and/or $t_3$.

Preferably, the lower limit for the oxygen flow rate during a treatment phase, $t_1$, $t_2$ and/or $t_3$ comprises a lower minimum short-term oxygen flow rate and a lower minimum long-term oxygen flow rate.

Preferably, the upper limit for the oxygen flow rate during a treatment phase, $t_1$, $t_2$ and/or $t_3$ comprises a lower maximum sort-term oxygen flow rate and an upper maximum long-term oxygen flow rate.

For use with the present method (20) and device (10) of the invention, input patient data may comprise patient data for patient maximum and minimum average $SpO_2$ during one or more of $t_1$, $t_2$ and/or $t_3$. Further, patient data, preferably input patient data, may comprise a hazard level of average patient $SpO_2$ and/or a critical level of average patient $SpO_2$.

In the art, the hazard level is often taken to be 94-97% of minimum average patient $SpO_2$, and/or the critical level is taken to be 80% of minimum average patient $SpO_2$. It is for the medical practitioner to determine for a given patient critical and hazard levels of minimum average $SpO_2$ for a given patient. In embodiments of the invention, the controller (13) is configured for receiving, preferably receiving as input patient data, requisite hazard and/or critical levels of average patient $SpO_2$ during any of the treatment phases, $t_1$, $t_2$ and/or $t_3$.

In embodiments, the controller is set to adjust the flow rate of oxygen to either the maximum long-term or short-term flow rate, respectively, if the average patient $SpO_2$ during either of $t_1$ or $t_2$ subceeded the aforementioned hazard or critical average patient $SpO_2$-levels.

Without being bound by any theory, the present inventors have made the observation that iterative $O_2$-treatment as performed with the double closed-loop regulated devices (1) for automated oxygen therapy of the prior art is not sufficiently predictive over long times (hours) for stable automated oxygen therapy without patient monitoring. Surprisingly, the present inventors have observed that the reduced predictive value of the iterative $O_2$-treatment in many situations is due to low patient stability to $O_2$-treatment during the initial iterative $O_2$-treatment of the prior art. The present invention utilizes this insight to include a first set time for monitoring, in some embodiments for monitoring and stabilization of $O_2$-treatment, $t_1$, prior to a variable second set time $O_2$-treatment, $t_2$, where $O_2$-treatment is adapted to the physiological data measured in $t_1$ and $t_2$. During both of these time periods, the patient measures physiological data with a sensor (3), for predicting a third set time for long-term treatment, $t_3$, during which the patient does not measure his or her physiological data. Overall, the sum of $t_1+t_2<t_3$, but usually and preferred $t_1+t_2\ll t_3$.

Figure 4A:
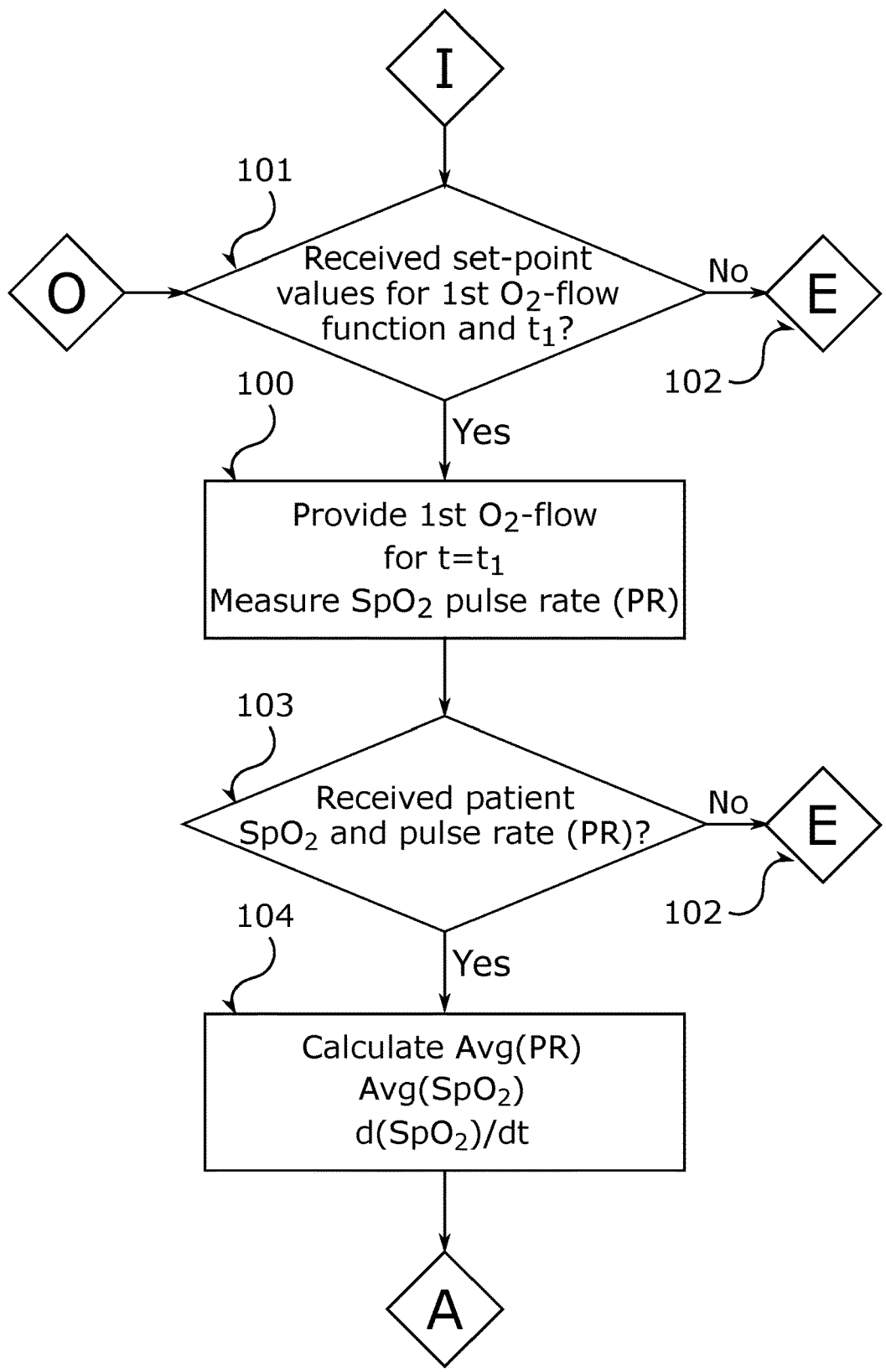
FIG. 4A: Flowchart for automated home oxygen therapy (A)

In FIG. 4A is shown an exemplary flowchart for a first part (A) of the method (20) of automated oxygen therapy according to the invention.

In accordance with the method (20) for providing automated oxygen therapy to a patient (4) of invention, the patient (4) is provided (100) with a first flow of oxygen for a first set time $t_1$. As mentioned, providing a first flow of oxygen for a first set time $t_1$ serves the aim of monitoring, in some embodiments stabilizing and monitoring, the patient vis-à-vis the effects of an initial $O_2$-treatment.

In accordance with the method (20) a patient (4) shall be provided (100) with a first flow of oxygen for a first set time, $t_1$, during which time, $t_1$, it is necessary for the patient receiving treatment to wear a sensor (3) providing patient physiological data to the controller (13). Accordingly, in one embodiment, the controller (13) is configured to receive patient physiological data during $t_1$, and to return an error (102) of process if not received.

Typically, and preferred, the first set time, $t_1$, for the first measuring phase does not exceed 15 minutes, does not exceed 10 minutes, does not exceed 9 minutes, does not exceed 8 minutes, does not exceed 7 minutes, preferably does not exceed 6 minutes, and more preferably does not exceed 5 minutes.

Generally, short lengths of first set time, $t_1$, for the first measuring phase are preferred for patient comfort. In preferred embodiments, the first set time, $t_1$, is 10 minutes, 9 minutes, 8 minutes, 7 minutes, preferably 6 minutes, and more preferably 5 minutes or 4 minutes. Shorter values for the first set time, $t_1$, are possible; however, this increases the risk that the first measuring phase becomes too short for obtaining reliable physiological data on a measured patient during $t_1$.

In order to monitor, respectively stabilize and monitor, the initial $O_2$-treatment to the patient, the first flow of oxygen preferably is not delivered as an iterative flow of oxygen in accordance with the prior art. Rather, the first flow of oxygen can be a variable or constant first flow of oxygen but not iterative with feedback from the sensor (3) to the controller (13) for regulating the flow of oxygen.

In accordance with the method (20) of the invention, a first set of patient physiological data comprising patient $SpO_2$ and pulse rate shall be measured for a patient by use of the sensor (3) during provision (100) of the first flow of oxygen for duration of at least a part of the first set time, $t_1$, preferably for duration of the entire first set time, $t_1$.

In an embodiment of the method (20) and device (10) of the invention, the controller (13) is configured for receiving (101) first set-point values establishing the aforementioned first set time, $t_1$, an initial first flow of oxygen, and a function establishing the first flow of oxygen as a function of the first set time, $t_1$, which can be variable or constant with the first set time, $t_1$. In event of the controller (13) not receiving the necessary set-point values, the controller (13) is configured for returning an error (102) of process.

A constant first flow of oxygen is generally most suitable for use in providing oxygen to a patient, whereas a variable first flow of oxygen is generally less suitable for providing a stable measuring phase.

Accordingly, it is preferred in the method (20) of the invention to set values or to receive (101) set-point values as first set-point values for the first flow of oxygen and $t_1$ such that oxygen is delivered essentially as a constant set flow of oxygen over the entire length of $t_1$. Thereby the measured physiological data for a patient being measured become more representative for the actual physiological state of the patient during $t_1$ than when the flow of oxygen is varied or adapted. However, in some cases it is necessary to allow a first flow of oxygen, which is variable during a subset, $t_1'$, of $t_1$. As mentioned, this will typically be the case, when treatment according to the method (20) of the invention is initialized or has been interrupted by the patient removing the oxygen delivery means (6) etc. In such situations, there can be a need to convergent vary the first flow of oxygen from an initial flow of oxygen towards a set constant first flow of oxygen in order to compensate for saturation effects of a patients physiological data influencing stable measurement of $SpO_2$ and pulse rate (PR).

In general, two situations <I> and <O> can be discerned for receiving the set-point values necessary for providing a first oxygen flow for a first set time, $t_1$, cf. FIG. 4A.

In some embodiments corresponding to situation <I>, the set-point values can be received as initial values at start of treatment as input patient data for treatment patient data provided by health care personnel via a patient data input means (18) optionally comprised in the device (10) of the invention.

In the second situation <O>, the patient receiving treatment has already completed one treatment cycle, $t_1+t_2+t_3$, and is initiating a further treatment cycle. Here, it is advantageous to continue using the oxygen flow setting used during the oxygen administration period defined by the third set time, $t_3$. Thereby the patient's physiological data will already be stable at the set flow of oxygen, improving the reliability of the measurements during $t_1$. Further, in situation <O> it will not generally be necessary for health care personnel to input a new set-point value for $t_1$, rather a fixed value for $t_1$ can be used, as detailed above, thereby minimizing personnel resources.

Irrespective thereof and in accordance with the invention, the first set flow of oxygen shall fall within the set limits for the minimum and maximum long-term oxygen flow rate during $t_1$. If in situation <O> the oxygen flow at the end of a first treatment cycle is not within the above limits, the oxygen flow rate will be adjusted by the controller to fall within the set limits. During adjustment, patient $SpO_2$ and pulse rate in preferred embodiments are measured rather than only during constant oxygen flow.

In an embodiment of the method (20) and device (10) of the invention, the controller (13) is configured for confirming (103) if a first set of physiological data comprising patient $SpO_2$ and pulse rate were received from a sensor (3) operatively connected to the controller (13) and to return an error (102) of process if not.

In an embodiment of the method (20) and device (10) of the invention, the controller (13) is configured for calculating (104) an average pulse rate, an average $SpO_2$ and $d(SpO_2)/dt$ as a first set of physiological data comprising patient $SpO_2$ and pulse rate received from a sensor (3) operatively connected to the controller (13).

Figure 4B:
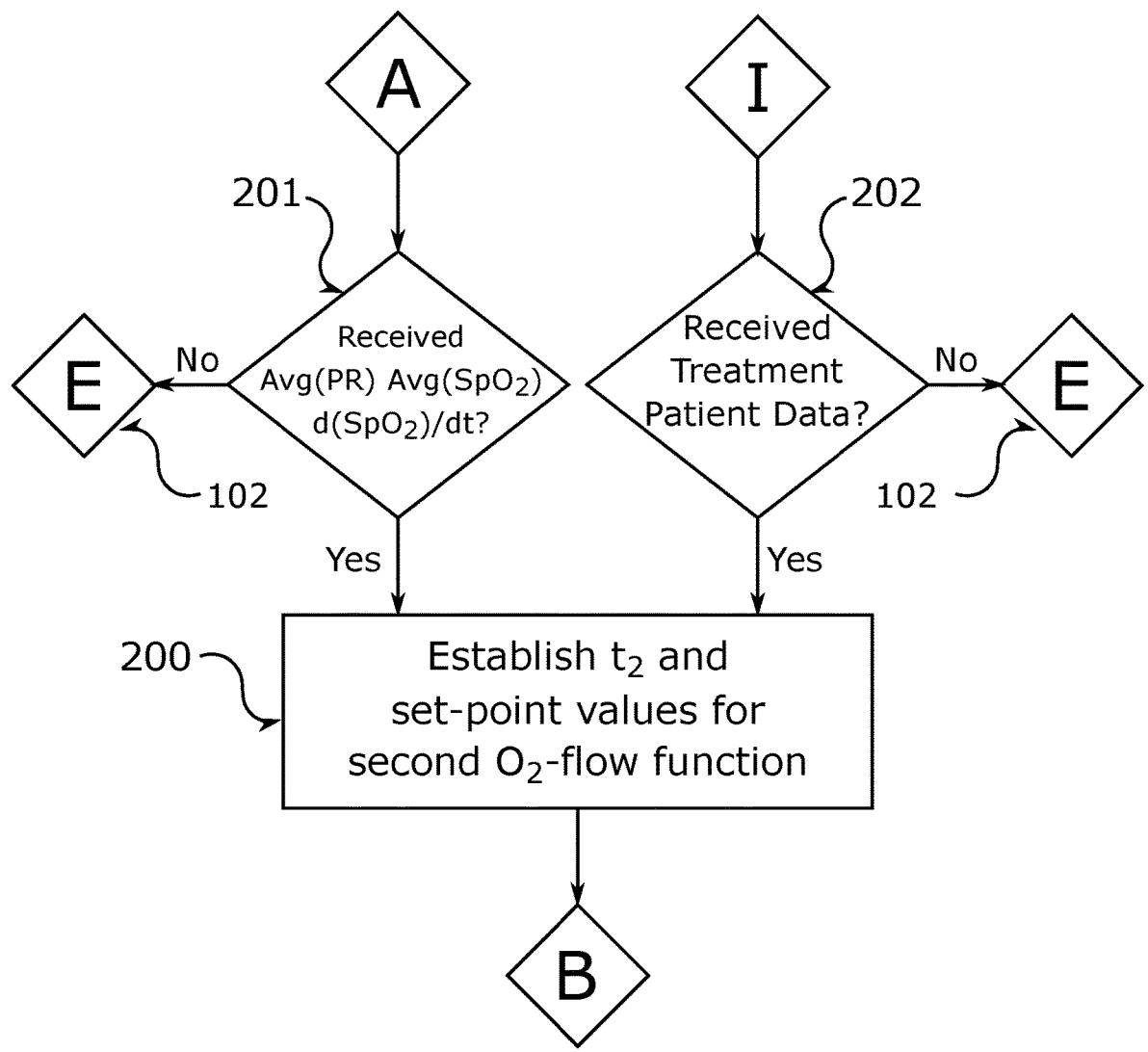
FIG. 4B: Flowchart for automated home oxygen therapy (B)

In FIG. 4B is shown an exemplary flowchart for a second part (B) of the method (20) of automated home oxygen therapy according to the invention.

In accordance with the method (20) for providing automated oxygen therapy to a patient (4) of invention, the patient (4) shall be provided (300) with a variable second flow of oxygen for a second set time $t_2$. As mentioned, providing a variable, preferably an iterative, second flow of oxygen for a second set time $t_2$ serves the aim of establishing a predictive flow of oxygen for automated $O_2$-treatment to the patient during the third set time, $t_3$.

Ideally, the oxygen flow obtained by iteration by measuring the patient's physiological data in $t_2$ is the oxygen flow, which brings the physiological data within a predefined acceptable range of oxygen flow during $t_2$, as determined by the received input patient date for patient maximum and minimum average $SpO_2$ during one or more of $t_2$ without violating the predefined limits for maximum and minimum long-term oxygen flow rate during $t_2$ or during treatment in $t_3$. Under less ideal circumstances, limits for oxygen flow can be exceeded during $t_2$, in which case the oxygen flow during $t_3$ will be adjusted, preferably the oxygen flow during $t_3$ will be gradually adjusted to be within the predefined limits for maximum and minimum long-term oxygen flow rate during $t_2$ or during treatment in $t_3$, and $t_3$ will be shortened to reflect that acceptable oxygen flow range is not sufficient to maintain a desired level of the physiological data, as will be further detailed below.

Typically, and preferred, the second set time, $t_2$, does not exceed 30 minutes, does not exceed 25 minutes, does not exceed 22 minutes, does not exceed 20 minutes, does not exceed 19 minutes, does not exceed 18 minutes, does not exceed 17 minutes, preferably does not exceed 16 minutes, and more preferably does not exceed 15 minutes.

Generally, short lengths of second set time, $t_2$, for the second measuring phase are preferred for patient comfort. In preferred embodiments, the second set time, $t_2$, is 20 minutes, 19 minutes, 18 minutes, 17 minutes, preferably 16 minutes, and more preferably 15 minutes, 14 minutes, 13 minutes, 12 minutes, 11 minutes or 10 minutes. As will be detailed below, in some embodiments $t_2$, can be as short as 9 minutes, 8 minutes, 7 minutes, 6 minutes, 5 minutes, 4 minutes, 3 minutes or even 2 minutes.

Thereby, and following the invention, the total measurement period, $t_1+t_2$, which the patients must wear a sensor (3) during automated oxygen therapy is shortened significantly compared to the prior art of continuous double closed-loop regulated automated oxygen therapy. Preferably, the total measurement period, $t_1+t_2$, does not exceed 30 minutes, does not exceed 25 minutes, does not exceed 20 minutes, does not exceed 18 minutes, does not exceed 16 minutes, does not exceed 15 minutes, does not exceed 14 minutes, preferably does not exceed 12 minutes, and more preferably does not exceed 10 minutes. Thereby patient comfort is optimized by requiring only short total measuring periods where the patient has to be attached to the sensor (3).

In a preferred embodiment (200) of the method (20) and device (10) of the invention, the controller is configured for establishing (200) second set-point values for $t_2$ and/or for the second flow of oxygen based on received treatment patient data, the treatment patient data comprising expected patient physiological data and patient treatment data.

In a preferred embodiment (200) of the method (20) and device (10) of the invention, the controller is configured for establishing (200) second set-point values for $t_2$ and the initial second flow of oxygen based on a deviation in measured average $SpO_2$ in $t_1$ from acceptable $SpO_2$ values, $d(SpO_2)/dt$ during $t_1$, and deviation of average pulse rate from acceptable pulse rate.

In an embodiment (201) of the method (20) and device (10) of the invention, the controller (13) is configured for validating (201) that an average pulse rate, an average $SpO_2$ and $d(SpO_2)/dt$ for a first set of physiological data comprising patient $SpO_2$ and pulse rate received from the sensor (3) have been calculated (104) and received before $t_2$ is established, and to return an error (102) of process if not.

In an embodiment of the method (20) and device (10) of the invention, the controller (13) is configured (202) for confirming; that treatment patient data has been received, and to return an error (102) of process if not. In one embodiment, the treatment patient data comprises expected patient physiological data for acceptable $SpO_2$, acceptable average pulse rate, and/or acceptable $d(SpO_2)/dt$ during $t_1$, preferably comprises expected patient physiological data particular to a respective patient receiving respective treatment according to the respective treatment patient data.

In general, for receiving the set-point values necessary for providing a second oxygen flow for a second set time, $t_2$, cf. FIG. 4B, the necessary set-point values for $t_2$, and initial second oxygen flow before iteration can, in some embodiments, be input <I> by health care personnel using the patient data input means (18) comprised in the device (10) of the invention. In most embodiments, and preferably, the initial second oxygen flow before iteration will be the same as the first oxygen flow for assuring a gradual entry into the iterative regulation regime of oxygen during $t_2$.

However, while the length of the second set time, $t_2$, can be set by external input, in preferred embodiments, the length of the second set time, $t_2$, is established (200) using treatment patient data comprising expected patient physiological data for acceptable $SpO_2$, acceptable average pulse rate, and/or acceptable $d(SpO_2)/dt$ during $t_1$, and measured and/or calculated values for the same data obtained (201) from a process for calculating (104) an average pulse rate, an average $SpO_2$ and $d(SpO_2)/dt$ as a second set of physiological data comprising patient $SpO_2$ and pulse rate received from a sensor (3) operatively connected to the controller (13). Thereby an optimized, usually an optimized and shortened, second measurement period for the length of second set time, $t_2$, can be established.

Accordingly, it is intended in accordance with preferred embodiments of the invention, that treatment patient data comprising expected patient physiological data for acceptable $SpO_2$, acceptable average pulse rate, and/or acceptable $d(SpO_2)/dt$ during $t_2$, are input <I> by health care personnel using patient data input means (18) optionally comprised in the device (10) of the invention, prior to establishing the length of the second set time, $t_2$, and the initial second oxygen flow before iteration.

Figure 4C:
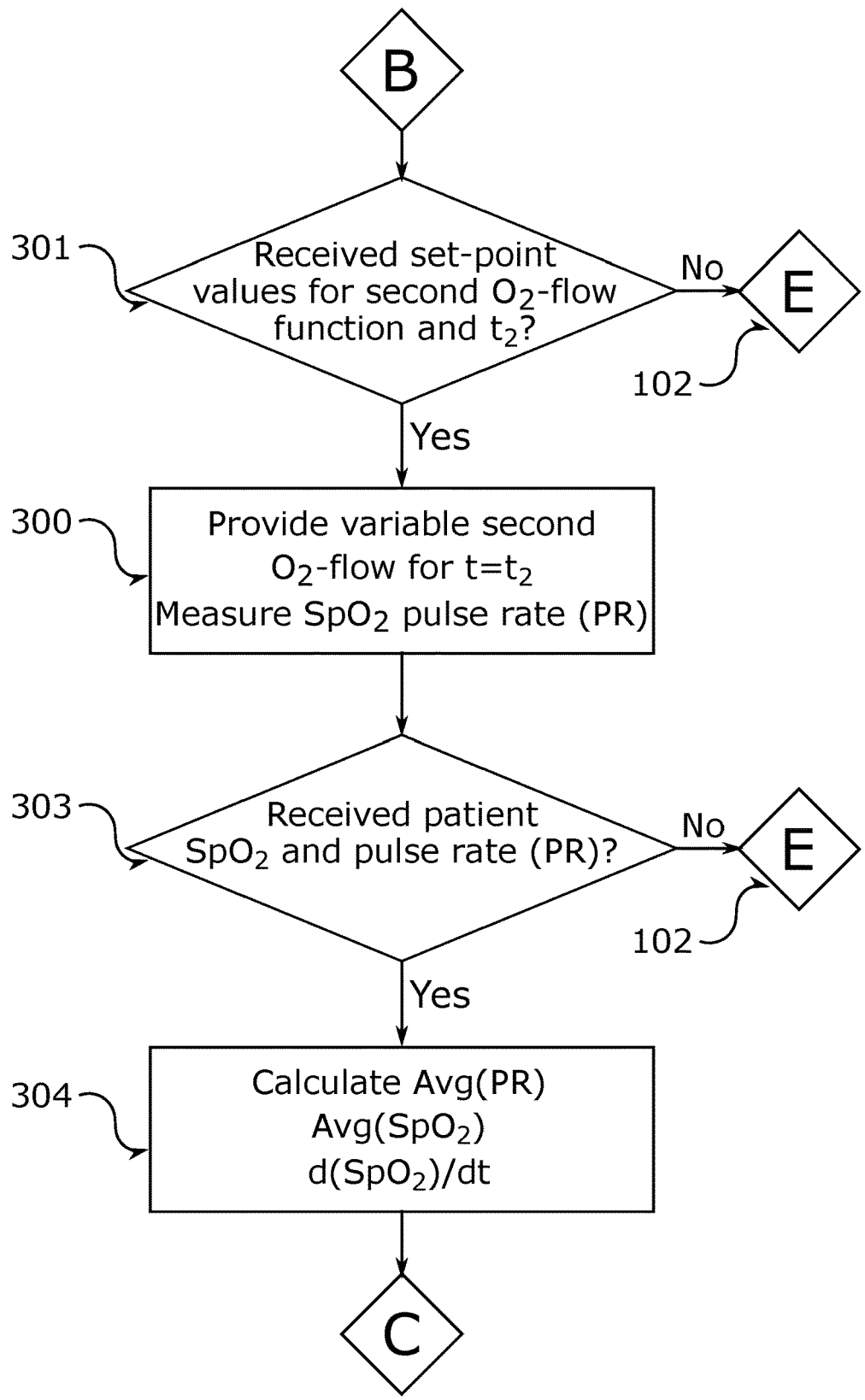
FIG. 4C: Flowchart for automated home oxygen therapy (C)

In FIG. 4C is shown an exemplary flowchart for a third part (C) of the method (20) of automated home oxygen therapy according to the invention.

In accordance with the method (20) a patient (4) shall be provided (300) with a second flow of oxygen for a second set time, $t_2$, during which time, $t_2$, it is necessary for the patient receiving treatment to wear a sensor (3) providing patient physiological data to the controller (13). Accordingly, in one embodiment, the controller (13) is configured for receiving patient physiological data during $t_2$, and to return an error (102) of process, if not received.

In an embodiment (301) of the method (20) and device (10) of the invention, the controller (13) is configured for receiving (301) second set-point values establishing the second set time, $t_2$, an initial second flow of oxygen, and a function establishing the second flow of oxygen as a function of the second set time, $t_2$, which can be variable or iterative with the second set time, $t_2$. In event of the controller (13) not receiving the necessary set-point values, the controller (13) is configured for returning an error (102) of process. Preferably, the second set-point values are received from a process (200) for establishing second set-point values for the second set time, $t_2$, an initial second flow of oxygen, and a function establishing the second flow of oxygen as a function of the second set time, $t_2$.

In accordance with the method (20) of the invention, in some embodiments the provided (300) variable second flow of oxygen can be a convergent variable flow of oxygen, wherein the flow of oxygen converges towards a substantially constant flow of oxygen. This is typically advantageous when the device (10) has detected an error (102) of process, such as e.g. a failure to obtain physiologically meaningful physiological patient data. In such cases, it can be necessary to maintain a preset default second flow of oxygen during $t_2$, which may be different from the initial second flow of oxygen and therefore requiring adjusting the flow of oxygen before using, until e.g. contacted authorized health care personnel or the patient has had time to correct detected errors of process.

However, it is intended and preferred in embodiments of the method (20) of the invention that the provided (300) variable second flow of oxygen shall be an iterative second flow of oxygen, wherein the controller (13) iteratively regulates, using feedback (16,31) from the flowmeter (12) and the sensor (3), the second flow of oxygen during $t_2$ until a substantially stable second flow of oxygen can be provided, preferably a substantially stable second flow of oxygen corresponding to treatment patient data. Preferably, the stable second flow of oxygen is a substantially constant flow of oxygen.

In accordance with the method (20) of the invention, a second set of patient physiological data comprising patient $SpO_2$ and pulse rate shall be measured for a patient by use of the sensor (3) during provision (300) of the second flow of oxygen for duration of at least a part of the second set time, $t_2$, preferably for duration of the entire second set time, $t_2$.

In an embodiment of the method (20) and device (10) of the invention, the controller (13) is configured for confirming (303) if a second set of patient physiological data comprising patient $SpO_2$ and pulse rate were received from a sensor (3) operatively connected to the controller (13) and to return an error (102) of process if not.

In an embodiment of the method (20) and device (10) of the invention, the controller (13) is configured for calculating (304) an average pulse rate, an average $SpO_2$ and $d(SpO_2)/dt$ as a second set of physiological data comprising patient $SpO_2$ and pulse rate received from the sensor (3).

Figure 4D:
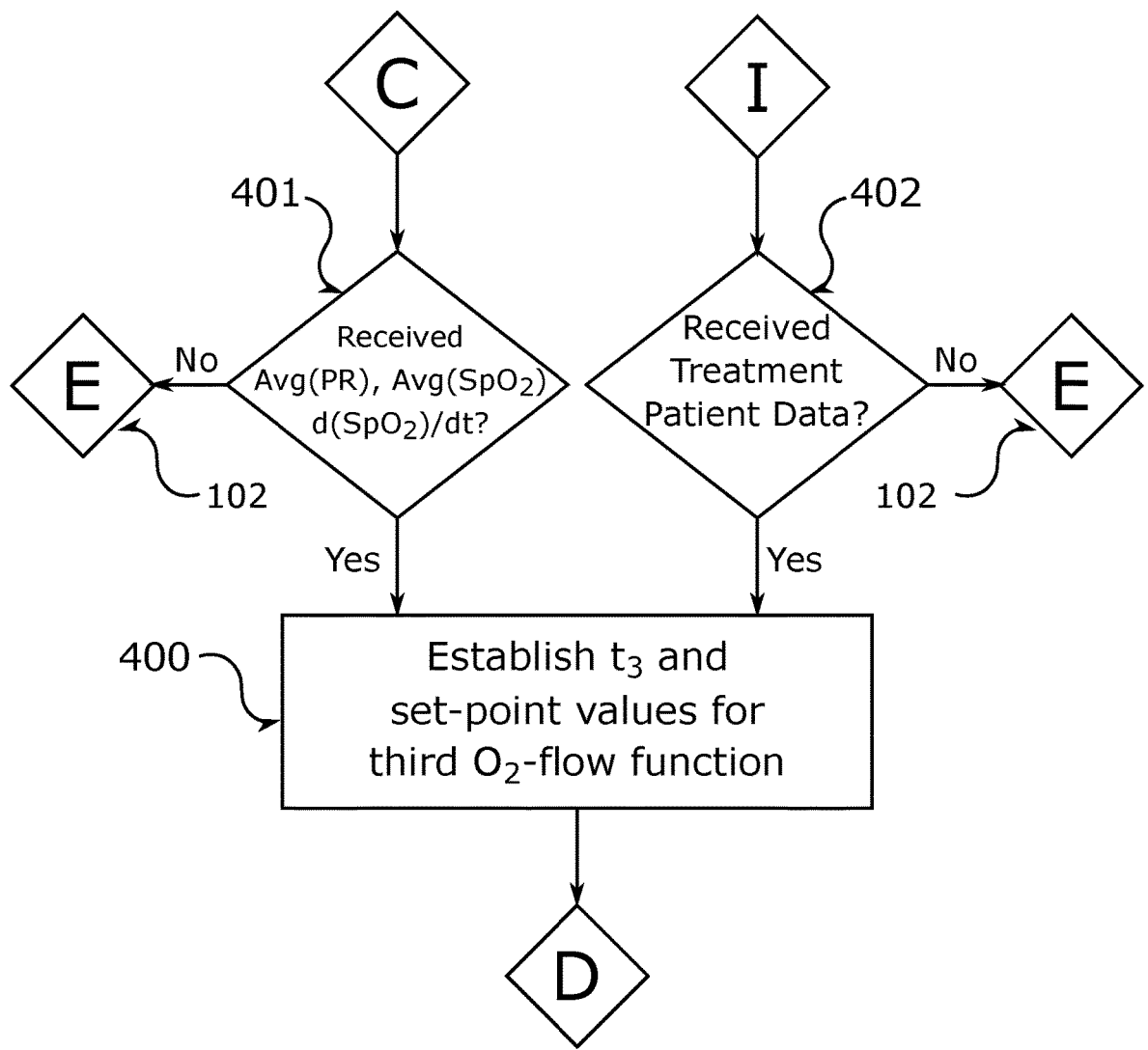
FIG. 4D: Flowchart for automated home oxygen therapy (D)

In FIG. 4D is shown an exemplary flowchart for a fourth part (D) of the method (20) of automated home oxygen therapy according to the invention.

In accordance with the method (20) for providing automated oxygen therapy to a patient (4) of invention, the patient (4) shall be provided (500) with a third flow of oxygen for a third set time, $t_3$, during which time, $t_3$, it is not necessary for the patient receiving treatment to wear a sensor (3) providing patient physiological data to the controller (13).

Typically, and preferred, the third set time, $t_3$, does not exceed 24 hours, does not exceed 18 hours, does not exceed 16 hours, preferably does not exceed 14 hours, and more preferably does not exceed 12 hours.

Typically, and preferred, the third set time, $t_3$, permits a thrice daily measurement period, $t_1+t_2$, more preferably permits a twice daily measurement period, $t_1+t_2$, or even more preferably permits a once daily measurement period, $t_1+t_2$.

Typically, and preferred, the third set time, $t_3$, is not shorter than 1 hour, is not shorter than 2 hours, is not shorter than 3 hours, is not shorter than 4 hours, and more preferably is not shorter than 5 hours.

In accordance with the method (20) of the invention, the third set time, $t_3$, being the treatment time without associated measuring of patient physiological data is not shorter than around 1 hour, when shortest. In general, $t_3$ will be of a length permitting a patient to experience sufficiently long periods without having to measure his or hers physiological data while still receiving adequate oxygen therapy. In preferred embodiments, if $t_3$ becomes too short, e.g. such as shorter than 1 hour, as established with basis in the patient's physiological data obtained from the sensor (3), the controller is configured for notifying authorized health care personnel.

As mentioned, in one embodiment of the notification means (17) configured for providing a notification in the event of an error (102) of process, the notification means (17) are configured (17a) for contacting authorized health care personnel. In one embodiment thereof, the notification means (17) are configured (17a) for contacting authorized health care personnel if the value of the third set time, $t_3$, is below a given value of $t_3$ for notification as an error (102) of process. Preferably, the value of $t_3$ for notification is set by authorized health care personnel based on an individual assessment of a given patient. However, for reasons of safety, the notification means (17) should be configured (17a) for contacting authorized health care personnel using also a pre-set and fixed lower value of $t_3$ for notification, thereby preventing an accidental setting of the value of $t_3$ for notification by health care personnel, which is too long. As such, preferably the notification means (17) are configured for permitting authorized health care personnel only to set a value of $t_3$ for notification, which is lower than the pre-set and fixed lower value of $t_3$ for notification.

In a preferred embodiment (400) of the method (20) and device (10) of the invention, the controller is configured for establishing (400) third set-point values for $t_3$ and/or for the third flow of oxygen based on received treatment patient data, the treatment patient data comprising expected patient physiological data and patient treatment data.

In a preferred embodiment (400) of the method (20) and device (10) of the invention, the controller is configured for establishing (400) third set-point values for $t_3$ and/or for the third flow of oxygen based on deviation of average $SpO_2$ in $t_2$ from acceptable $SpO_2$ and deviation of oxygen flow at end of $t_2$ from acceptable oxygen flow.

In an embodiment (401) of the method (20) and device (10) of the invention, the controller (13) is configured for validating (401) that an average pulse rate, an average $SpO_2$ and $d(SpO_2)/dt$ for a second set of physiological data comprising patient $SpO_2$ and pulse rate received from the sensor (3) have been calculated (304) and received before $t_3$ is established, and to return an error (102) of process if not.

In an embodiment of the method (20) and device (10) of the invention, the controller (13) is configured (402) for confirming; that treatment patient data has been received, and to return an error (102) of process if not. In one embodiment, the treatment patient data comprises expected patient physiological data for acceptable $SpO_2$, acceptable average pulse rate, and/or acceptable $d(SpO_2)/dt$ during $t_2$, preferably comprises expected patient physiological data particular to a respective patient receiving respective treatment according to the respective treatment patient data.

In general, for receiving the set-point values necessary for providing a third oxygen flow for a third set time, $t_3$, cf. FIG. 4D, the necessary set-point values for $t_3$, and initial third oxygen flow before oxygen delivery without associated measuring of patient physiological data can, in some embodiments <I>, be input by health care personnel using patient data input means (18) optionally comprised in the device (10) of the invention. In most embodiments, and preferably, the initial third oxygen flow before oxygen delivery without associated measuring of patient physiological data will be the same as the resulting second oxygen flow after iteration for assuring a gradual entry into the regulation regime of oxygen without associated measuring of patient physiological data during $t_3$.

Accordingly, it is intended in embodiments of the invention, that treatment patient data comprising expected patient physiological data for acceptable $SpO_2$, acceptable average pulse rate, and/or acceptable $d(SpO_2)/dt$ during $t_2$, are input <I> by health care personnel using patient data input means (18) optionally comprised in the device (10) of the invention, prior to establishing the length of the third set time, $t_3$, and the third oxygen flow before oxygen treatment without associated monitoring.

In embodiments where it is intended to receive input patient data for treatment patient data by input <I> from health care personnel using the optionally comprised patient data input means, it is advantageous to receive all input patient data in a single input sequence, such as receiving all input patient data prior to providing the first oxygen flow for the first set time, $t_1$. Thereby handling time by health care personnel is minimized to single actions, such as only at initiation of treatment cycle, $t_1+t_2+t_3$, or only at initiation and/or completion of each treatment cycle, $t_1+t_2+t_3$.

In embodiments, where health care personnel are required to provide input patient data for treatment patient data, it is preferable to provide patient data input means (18) comprising selection means, preferably comprising selection means comprising a selection menu, comprising preset patient treatment input patient data for selecting by health care personnel as input patient data for treatment patient data. Thereby risks of accidentally setting patient treatment data outside suitable clinical limits can be minimized. The design and operation of such selection means comprised in patient data input means (18) are well-known in the art and outside the scope of the present invention.

However, while the length of the third set time, $t_3$, can be set by external input, in preferred embodiments, the length of the third set time, $t_3$, is established (400) using treatment patient data comprising expected patient physiological data for acceptable $SpO_2$, acceptable average pulse rate, and/or acceptable $d(SpO_2)/dt$ during $t_3$, and measured and/or calculated values for the same data obtained (301) from a process for calculating (304) an average pulse rate, an average $SpO_2$ and $d(SpO_2)/dt$ as a third set of physiological data comprising patient $SpO_2$ and pulse rate received from a sensor (3) operatively connected to the controller (13). Thereby an optimized treatment period and third oxygen flow for the length of third set time, $t_3$, can be established.

Figure 4E:
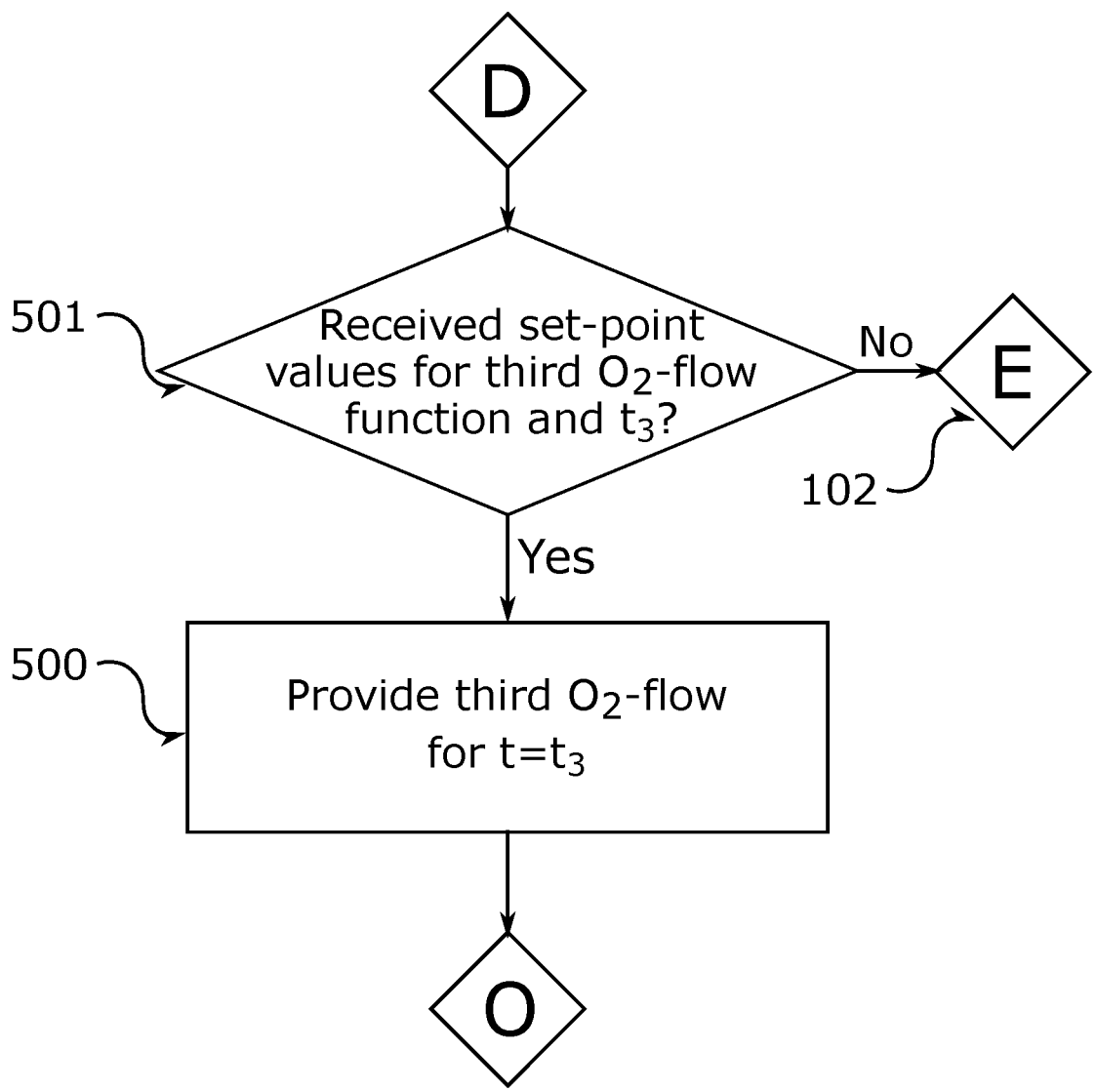

In FIG. 4E is shown an exemplary flowchart for a fifth part (E) of the method (20) of automated home oxygen therapy according to the invention.

In accordance with the method (20) a patient (4) shall be provided (500) with a third flow of oxygen for a third set time, $t_3$, during which time, $t_3$, it is not necessary for the patient receiving treatment to wear a sensor (3) providing patient physiological data to the controller (13). Accordingly, in one embodiment, the controller (13) is configured not to receive patient physiological data during $t_3$, and to return an error (102) of process if received.

In an embodiment (501) of the method (20) and device (10) of the invention, the controller (13) is configured for receiving (501) third set-point values establishing the third set time, $t_3$, an initial third flow of oxygen, and a function establishing the third flow of oxygen as a function of the third set time, $t_3$, which function can be variable or constant with the third set time, $t_3$. In event of the controller (13) not receiving the necessary set-point values, the controller (13) is configured for returning an error (102) of process. Preferably, the third set-point values are received from a process (400) for establishing third set-point values comprising a third set time, $t_3$, an initial third flow of oxygen, and a function establishing the third flow of oxygen as a function of the third set time, $t_3$.

In accordance with the method (20) of the invention, in an embodiment the provided (500) third flow of oxygen can be a convergent variable flow of oxygen, wherein the third flow of oxygen converges towards a substantially constant third flow of oxygen. This is typically used when the second flow of oxygen is different from the established third flow of oxygen. However, in other embodiments the established third flow of oxygen is a substantially constant third flow of oxygen.

In accordance with the invention, there is further detailed herein the use of a double closed-loop regulated device (10) for regulating a flow of oxygen for automated oxygen therapy according to any of the herein detailed embodiments for use in a method for providing automated oxygen therapy to a patient (4) according to any of the herein detailed methods.

In accordance with the invention, there is further detailed herein a double closed-loop regulated device (10) for regulating a flow of oxygen for automated oxygen therapy according to any of the herein detailed embodiments for use in a method for providing automated oxygen therapy to a patient (4) according to any of the herein detailed methods.

BEST MODE OF PRACTICE

While the present invention can be implemented in numerous manners, the present inventors have observed that by implementing, based on received treatment patient data, the processes (200,400) for establishing (200) second set-point values for the second set time, $t_2$, and/or for the second flow of oxygen and/or for establishing (400) third set-point values for the third set time, $t_3$, and/or for the third flow of oxygen as detailed herein below, there can be provided particularly suitable and simple implementations of the method (20) of the invention on the device (10) of the invention, the implementations having a very good reliability for a patient receiving automated home care therapy treatment during a given treatment cycle, $t_1+t_2+t_3$.

As is evident from the discussions of the invention above, the processes for establishing (200,400) second and/or third set-point values can be performed independently, relying only on measured and expected patient physiological data obtained during a previous set time and the associated respective separate measuring phase. Accordingly, the herein in this section presented processes for establishing (200,400) second and/or third set-point values can be independently implemented and accordingly, if a different process for establishing (200,400) second and/or third set-point values is used, combined independently with such a different process (200,400). In the present disclosure of a best mode of practice, the herein presented processes for establishing (200,400) second and/or third set-point values are used in combination.

Accordingly, in embodiments detailing a best mode of practice of the invention (20), a process for establishing (200) second set-point values for the second set time, $t_2$, and/or for the second flow of oxygen can be performed in accordance with the exemplary disclosure detailed in FIG. 5 and equations given herein below.

In accordance with the embodiments detailing a best mode of practice, input are received (200a) from processes (201) and (202) and $t_2$ (200b-f) and set-point values for the second oxygen flow (200g) are established and provided (200h) for use in further processes <B> of the method of the invention (20).

In accordance with a best mode of practice, the second set time, $t_2$, can be established (200b-f) in accordance with equation (1):

$$t_2 = t_2(\min) + t_2(SpO_2) + t_2(PR) + t_2(d(SpO_2)/dt) \quad (1):$$

wherein $t_2(\min)$ is a suitable minimum set time $t_2$, necessary for obtaining an iterated second oxygen flow during $t_2$. $t_2(\min)$ can in some embodiments (200b) be as short as 1 or 2 minutes, but is usually longer, such as up to 5 minutes. The necessary minimum second set time, $t_2(min)$, can be a fixed value comprised in received patient treatment data or stored in a memory unit (19) operatively connected to the controller.

In the herein suggested best mode of practice, the individual contributions (200c-e) from $SpO_2$, pulse rate (PR) and $d(SpO_2)/dt$ can be determined in accordance with equations (2) to (7):

To determine the contribution (200c) from the average $SpO_2$ during $t_1$ to $t_2$, equations (2) and (3) can be suitable:

$$\left| \frac{Avg(SpO_2 \text{ during } t_1) - \text{Acceptable } (SpO_2 \text{ during } t_1)}{\text{Acceptable } (SpO_2 \text{ during } t_1)} \right| \leq \Delta SpO_2(1+x), \quad (2)$$

$$x = 0, 1, 2, 3, 4, \ldots$$

wherein x is increased until equation (1) is true, whereupon:

$$t_2(SpO_2) = x * \Delta t \quad (3):$$

Herein $\Delta t$ is a suitable, clinically relevant, time increment, normally provided as part of a patient treatment data, but can also be a preset time increment. Typically, $\Delta t$ will be between minute to 5 minutes, such as 1 minute, 2 minutes, or 3 minutes. In some embodiments, a single value for $\Delta t$ is replaced with individual values for $\Delta t$ respective to each of equations (3), (5) and/or (7).

In relation to the presented best mode of practice, $\Delta SpO_2$ is a suitably small, clinically relevant, confidentiality interval for $SpO_2$, normally provided as part of a patient treatment data, but can also be a preset $\Delta SpO2$-interval. Typically, the $\Delta SpO2$-interval will be between 0.5% to 5%, such as 1%, 2% or 3%.

To determine the contribution (200d) from the average pulse rate during $t_1$ to $t_2$, equations (4) and (5) can be suitable:

if $Avg(PR) \leq Max(Acceptable(PR))$ then $x=0$ otherwise $x=1$     (4):

$$t_2(PR) = x * \Delta t \quad (5):$$

To determine the contribution (200e) from $d(SpO_2)/dt$ during $t_1$ to $t_2$, equations (6) and (7) can be suitable:

$$\text{if } \left| \frac{(d(SpO_2)/dt \text{ during } t_1) - \text{Acceptable } (d(SpO_2)/dt \text{ during } t_1)}{\text{Acceptable } (d(SpO_2)/dt \text{ during } t_1)} \right| \leq \Delta SpO_2 \quad (6)$$

then $x = 0$ otherwise $x = 1$ $$t_2(d(SpO_2)/dt) = x * \Delta t \quad (7)$$

Figure 5:
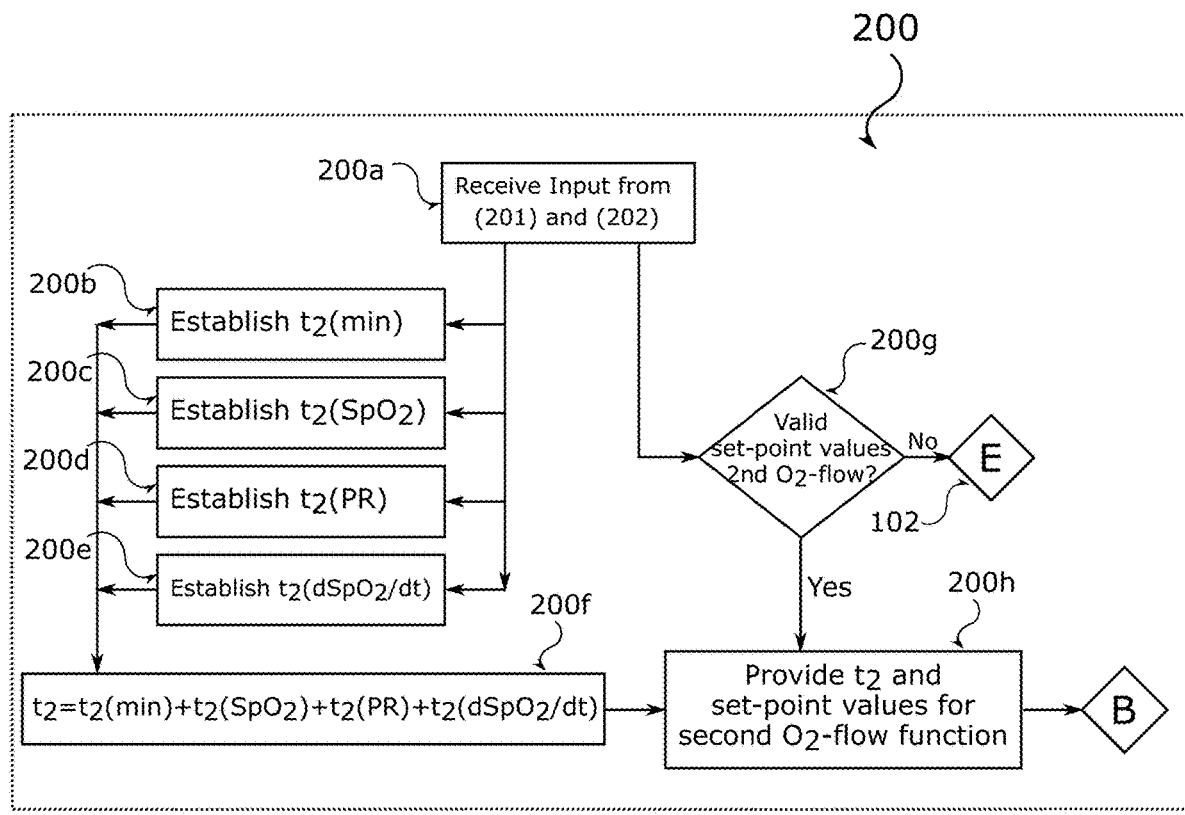
FIG. 5: Flowchart for best practice subroutine.

As can be seen from the above equations and illustrated in FIG. 5, the individual contributions to $t_2$ can be established independently of the other contributions, which is a particular benefit of the presented best mode of practice, making the calculations for establishing $t_2$ easier to implement on the controller (13) of the device (10) of the invention.

Further, in embodiments detailing a best mode of practice of the invention (20), a process for establishing (400) third set-point values for the third set time, $t_3$, and/or for the third flow of oxygen can be performed in accordance with the exemplary disclosure detailed herein below.

In accordance with the present inventors' suggested best mode of practice, $t_3$ is only set if, during $t_1$ and $t_2$, the flow rate of oxygen did not exceed the given maximum long-term oxygen flow rates. For safety, the controller (13) in a preferred embodiment is configured to restrict the oxygen flow rate not to exceed the set maximum short-term oxygen flow rate.

If the flow rate of oxygen during $t_1$ and $t_2$ exceeds these limits, the controller is configured in embodiments for notifying health care personnel and at the same time setting the flow of oxygen is to either the maximum long-term or short-term flow rate, respectively, if the average patient $SpO_2$ during either of $t_1$ or $t_2$ subceeded the aforementioned hazard or critical average patient $SpO_2$-levels.

If the average patient $SpO_2$ during $t_1$ and $t_2$ did not subceed the set minimum average patient $SpO_2$ hazard level but subceeded the minimum average patient $SpO_2$ level, $t_3$ is set to a shortened period, e.g. of 1 hours or 2 hours and the oxygen flow rate is set to the maximum long-term oxygen flow rate, after which time $t_3$ assessment in $t_1$ and $t_2$ is repeated.

If the flow rate of oxygen during re-evaluation during $t_1$ and $t_2$ did not subceed these limits, $t_3$ in some embodiments is set to thrice-daily measurement period $t_1 + t_2$.

In accordance with the present inventors' suggested best mode of practice, when $t_3$ is set, and when during $t_1$ and $t_2$, the flow rate of oxygen did not exceed the given maximum long-term oxygen flow rates, $t_3$ is set to permit either a twice daily or preferably, a once daily measurement period $t_1 + t_2$.

CLOSING COMMENTS

The term "comprising" as used in the claims does not exclude other elements or steps. The term "a" or "an" as used in the claims does not exclude a plurality. A single processor or other unit may fulfill the functions of several means recited in the claims. Although the present invention has been described in detail for purpose of illustration, it is understood that such detail is solely for that purpose, and variations can be made therein by those skilled in the art without departing from the scope of the invention.

The invention claimed is:

1. A double closed-loop regulated device for regulating a flow of oxygen for automated oxygen therapy, the device comprising an oxygen flow path for passing a flow of oxygen from a source of oxygen via the device for providing a controlled flow of oxygen, the device comprising a valve and a flowmeter arranged consecutively on the oxygen flow path, and a controller configured for controlling a provided flow of oxygen through the valve by adjusting the valve in response to feedback from the flowmeter and a sensor for measuring sets of physiological data comprising patient $SpO_2$ and pulse rate, the sensor configured for being operatively connected to the controller; the controller further configured for:

providing a first flow of oxygen for a first set time $t_1$ and, in response to a first set of physiological data comprising patient $SpO_2$ and pulse rate received from the sensor, establishing a second set time $t_2$;

providing a variable second flow of oxygen for the second set time $t_2$ while receiving a second set of physiological data comprising patient $SpO_2$ and pulse rate from the sensor;

establishing a third set time $t_3$ in response to the second set of physiological data received; and providing a third flow of oxygen for the third set time $t_3$ without receiving feedback from the sensor.

2. A double closed-loop regulated device for regulating a flow of oxygen for automated oxygen therapy according to claim 1, wherein $t_1+t_2<t_3$.

3. A double closed-loop regulated device for regulating a flow of oxygen for automated oxygen therapy according to claim 1, wherein the controller is configured for iteratively adjusting the variable second flow of oxygen for matching a received second set of physiological data comprising patient $SpO_2$ and pulse rate received from the sensor to a preset physiological data comprising patient $SpO_2$ and pulse rate.

4. A double closed-loop regulated device for regulating a flow of oxygen for automated oxygen therapy according to claim 1, the device further comprising the sensor operatively connected to the controller.

5. A double closed-loop regulated device for regulating a flow of oxygen for automated oxygen therapy according to claim 4, wherein the sensor is a pulse oximeter.

6. A double closed-loop regulated device for regulating a flow of oxygen for automated oxygen therapy according to claim 1, wherein the controller is configured for returning an error of process if a criterion for error of process is passed.

7. A double closed-loop regulated device for regulating a flow of oxygen for automated oxygen therapy according to the claim 1, wherein the device further comprises notification means operatively connected to the controller and configured for providing a notification if a criterion for error of process is passed.

8. A double closed-loop regulated device for regulating a flow of oxygen for automated oxygen therapy according to claim 1, wherein the device further comprises patient data input means operatively connected to the controller for permitting patient data to be provided to the controller for configuring the controller for establishing at least one value of $t$, $t_1$, $t_2$, or $t_3$ and/or for establishing at least one of a first, a second or a third flow of oxygen.

9. A double closed-loop regulated device for regulating a flow of oxygen for automated oxygen therapy according to claim 1, wherein the device further comprises a memory unit operatively connected to the controller for permitting provided patient data to be stored and accessed by the controller.

10. A double closed-loop regulated device for regulating a flow of oxygen for automated oxygen therapy according to claim 8, wherein the patient data comprises patient physiological data comprising patient $SpO_2$ and pulse rate.

11. A double closed-loop regulated device for regulating a flow of oxygen for automated oxygen therapy according to claim 1, wherein the first set time, $t_1$, does not exceed 15 minutes, does not exceed 10 minutes, does not exceed 9 minutes, does not exceed 8 minutes, does not exceed 7 minutes, preferably does not exceed 6 minutes, and more preferably does not exceed 5 minutes.

12. A double closed-loop regulated device for regulating a flow of oxygen for automated oxygen therapy according to claim 1, wherein the provided second flow of oxygen for the second set time, $t_2$, is an iterative second flow of oxygen during at least a part of the second set time, $t_2$.

13. A double closed-loop regulated device for regulating a flow of oxygen for automated oxygen therapy according to claim 1, wherein the second set time, $t_2$, does not exceed 30 minutes, does not exceed 25 minutes, does not exceed 22 minutes, does not exceed 20 minutes, does not exceed 19 minutes, does not exceed 18 minutes, does not exceed 17 minutes, preferably does not exceed 16 minutes, and more preferably does not exceed 15 minutes.

14. A double closed-loop regulated device for regulating a flow of oxygen for automated oxygen therapy according to claim 1, wherein a total measurement period, $t_1+t_2$, does not exceed 30 minutes, does not exceed 25 minutes, does not exceed 20 minutes, does not exceed 18 minutes, does not exceed 16 minutes, does not exceed 15 minutes, does not exceed 14 minutes, preferably does not exceed 12 minutes, and more preferably does not exceed 10 minutes.

15. A double closed-loop regulated device for regulating a flow of oxygen for automated oxygen therapy according to claim 1, wherein third set time, $t_3$, permits a thrice daily measurement period, $t_1+t_2$, more preferably permits a twice daily measurement period, $t_1+t_2$, or even more preferably permits a once daily measurement period, $t_1+t_2$.

16. A double closed-loop regulated device for regulating a flow of oxygen for automated oxygen therapy according to claim 1, wherein anyone of a first, a second and/or a third flow of oxygen does not exceed 5 l/min for more than 1 hour.

\* \* \* \* \*